United States Patent [19]

Andreiko

[11] Patent Number: 5,752,826
[45] Date of Patent: May 19, 1998

[54] DENTAL IMPRESSION TRAY AND HANDLE ASSEMBLY

[75] Inventor: Craig A. Andreiko, Alta Loma, Calif.

[73] Assignee: Ormco Corporation, Glendora, Calif.

[21] Appl. No.: 648,735

[22] Filed: May 16, 1996

Related U.S. Application Data

[63] Continuation-in-part of Ser. No. 341,508, Nov. 17, 1994, abandoned.

[51] Int. Cl.$^6$ ................................................ A61C 9/00
[52] U.S. Cl. ........................... 433/41; 433/46; 433/37
[58] Field of Search ..................... 433/37, 38, 41, 433/42, 43, 44, 45, 46, 47, 48

[56] References Cited

U.S. PATENT DOCUMENTS

| | | | |
|---|---|---|---|
| 987,063 | 3/1911 | Greene | 433/46 |
| 1,113,090 | 10/1914 | Bell | 433/46 |
| 1,127,635 | 2/1915 | Kerr | 433/46 |
| 1,323,832 | 12/1919 | Chige | 433/46 |
| 2,352,545 | 6/1944 | Jeffries | 433/47 |
| 2,577,513 | 12/1951 | Cunningham . | |
| 3,654,703 | 4/1972 | McAdoo . | |
| 4,227,877 | 10/1980 | Tureaud et al. | 433/37 |
| 4,445,854 | 5/1984 | Bekey et al. | 433/37 |
| 4,484,890 | 11/1984 | Jouvin | 433/37 |
| 4,530,662 | 7/1985 | Anderson | 433/37 |
| 5,076,785 | 12/1991 | Tsai | 433/46 |
| 5,336,086 | 8/1994 | Simmen et al. | 433/37 |
| 5,478,235 | 12/1995 | Schuldt et al. | 433/37 |

FOREIGN PATENT DOCUMENTS

| 2129818 | 12/1972 | Germany | 433/37 |
|---|---|---|---|

*Primary Examiner*—Cary E. O'Connor
*Attorney, Agent, or Firm*—Wood, Herron & Evans, L.L.P.

[57] ABSTRACT

A single use impression tray assembly has a dental impression tray (12, 100) with a separate but readily attachable handle (14, 114). Impression tray (12, 100) includes a handle securing element to selectively interlock handle (14, 114) to impression tray (12, 100). Additionally, impression tray (12, 100) includes a plurality of impression material retaining structure (68) for retaining impression material within the impression tray.

32 Claims, 4 Drawing Sheets

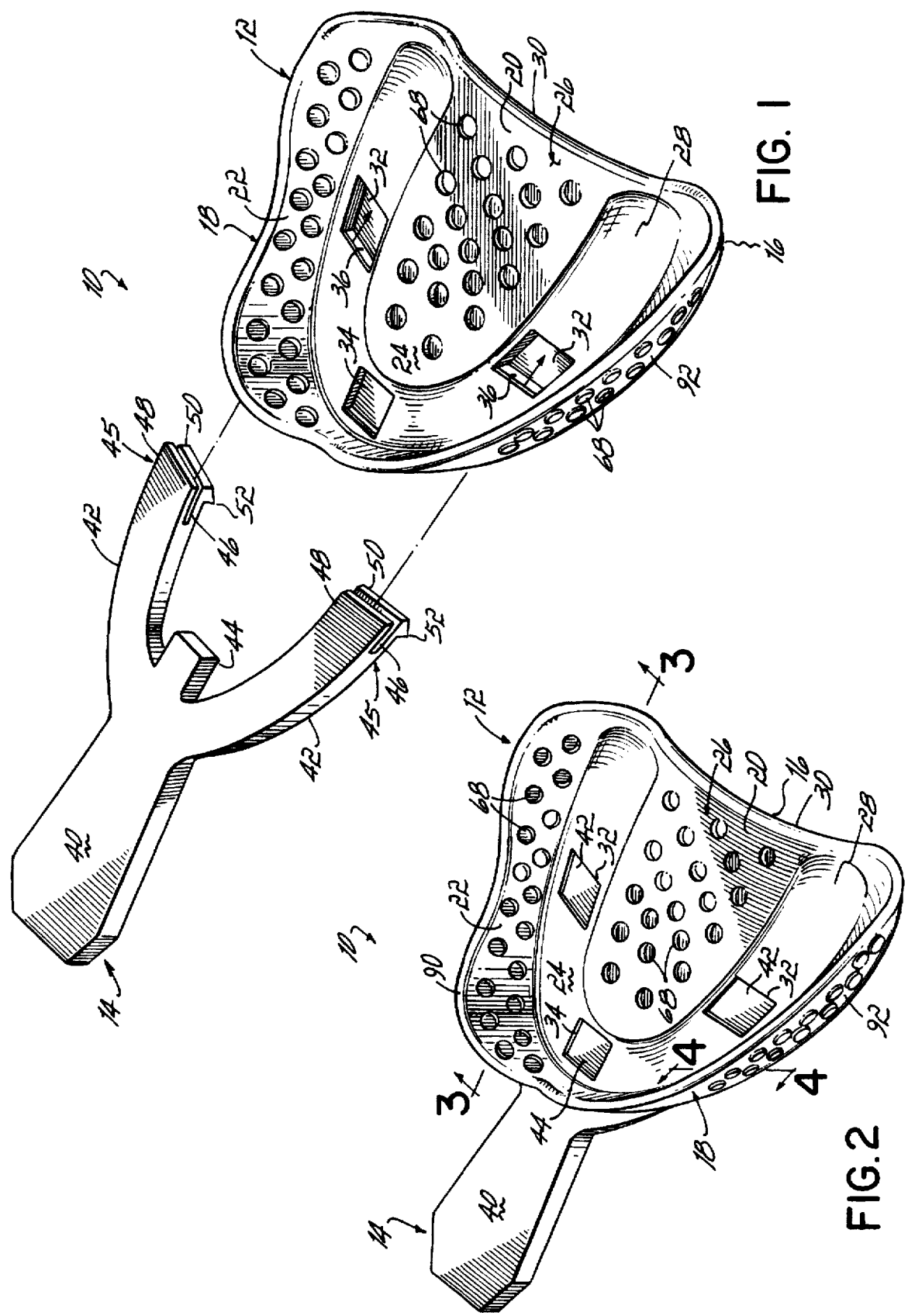

DENTAL IMPRESSION TRAY AND HANDLE ASSEMBLY

This is a continuation-in-part of application Ser. No. 08/341,508 filed Nov. 17, 1994, now abandoned.

FIELD OF THE INVENTION

The present invention relates generally to dental impression trays, and more particularly to a single use orthodontic impression tray adapted to retain the impression material in the tray when the tray is removed from the patient's mouth and having a separate, but readily attachable handle that is selectively interlocked to the impression tray.

BACKGROUND OF THE INVENTION

Many dental and orthodontic procedures require that an impression be formed of the patient's teeth either alone or in conjunction with the gums and vestibular anatomy. This impression is either used directly by the dentist or orthodontist to analyze the patient's mouth structure, or is used to form a plaster replica of the patient's teeth, gums, and vestibule. In either event, it is important that a good impression be formed in the first attempt, as the need to make a second impression necessitates additional visits by the patient, and costs the orthodontist and/or patient over $100 per incident.

Despite the desire for reliably forming good impressions on the first attempt, existing devices for use in making impressions suffer from various drawbacks. For example, existing smooth-sided metal and plastic trays are unable to retain the impression material within the tray when the tray is removed from the patient's mouth following formation of the impression. Specifically, as the impression material does not adhere to the sides of the impression tray, the impression material may adhere to the teeth or other oral anatomy when the tray is removed, which may result in damaging or destroying the impression. To overcome this drawback, contact cement spray must be applied to the surface of the impression tray prior to inserting the impression material therein to adhere the impression material to the tray. However, this is a messy procedure and often results in the contact cement inadvertently being applied to the user and/or his equipment.

Alternatively, some existing plastic impression trays include relatively large perforations therein to aid in adhering the impression material to the sides of the tray. However, these often fail to provide suitable impressions as the impression material may be forced through the large perforations rather than into the crevices of the mouth structure. In particular, the existing trays may fail to provide an adequate impression of the vestibular anatomy.

Additional drawbacks are also associated with existing impression trays. For example, existing plastic impression trays are not shapeable, and thus the dentist or orthodontist cannot conform the tray and impression material to the individual patient's anatomy during the impression forming procedure. Further, existing impression trays that include an integral handle cannot be readily stacked for convenient shipping and storage. Still further, existing impression trays having a separate handle are either cumbersome in use or the handle is not securely fastened to the impression tray.

Therefore, there is a significant need for an impression tray that includes structure for retaining the impression material therein and that avoids the drawbacks associated with the existing impression trays. Additionally, there is a need for a dental impression tray that does not include large perforations through which the impression material may be hydraulically forced and which is formable so that the impression tray may be formed to the contours of the patient's oral anatomy during the impression forming procedure. Finally, there is a need for an impression tray that is stackable for ease of shipping and storage and which includes a separate, but readily attachable handle.

SUMMARY OF THE INVENTION

The present invention provides a single use, dental impression tray and handle assembly which overcomes the drawbacks associated with the existing dental impression trays. More specifically, and in accordance with the present invention, a single use impression tray and handle assembly is provided. The impression tray includes a peripheral sidewall and a bottom, each having an interior surface, which together form the inside surface of the impression tray. The impression tray may be manufactured from a recyclable material that is manually deformable without the aid of tools during the impression procedure material and includes impression material retaining structure formed along the inside surface thereof to provide mechanical retention between the impression tray and the impression material. The impression tray may also include a separate, but readily attachable, handle that may be easily and selectively interlocked to the impression tray by dental office personnel immediately prior to use by a handle securing element, but which is otherwise unattached for compact shipping and storage.

The impression material retention structure may include a plurality of pockets formed along the inside surface of the impression tray, which serve to mechanically retain the impression material within the impression tray during the impression forming procedure. The pockets may have a substantially cylindrical configuration, and preferably include an undercut sidewall along with a concave base.

Alternatively, the impression material retention structure may comprise a plurality of fibers secured along the inside surface of the impression tray. These fibers may be electrostatically flocked and adhesively secured to the inside surface of the impression tray during the manufacturing process such that the fibers are oriented substantially perpendicular to the inside surface.

In a still further alternative, the impression material retention structure may comprise a plurality of apertures formed in the inside surface of the impression tray.

The handle securing element for selectively interlocking the impression tray and separate, but readily attachable, handle may include a plurality of tines on one of the handle and the impression tray with a plurality of mating stirrups on the other of the handle or impression tray. Preferably the tines are formed on the handle and the stirrups are formed on the impression tray. Thus, the stirrups may be formed by stamping a portion of the bottom of the impression tray a distance sufficient to receive the tines therebetween. Further, the stamped portions form apertures in the bottom of the impression tray which mate with the tines on the handles when the tines are inserted into the stirrups. The tines thus close off the apertures and prohibit the impression material from being hydraulically forced through the apertures during the impression forming process.

At least one of the tines may be resilient and include a detent adapted to releasably engage the stirrup when the tine is inserted therein.

Alternatively, a first tine of the plurality of tines may be positioned forwardly of a second tine, with the first tine extending forwardly and terminating in a leading edge and the second tine extending rearwardly and terminating in a trailing edge. The first tine is positioned to be received in a first stirrup and the second tine is positioned to be received in a second stirrup. Further, the distance between the leading edge and the trailing edge is greater than the smallest distance between said first stirrup and said second stirrup. Thus, to selectively interlock the handle and the impression tray, the first tine is inserted forwardly into the first stirrup until the trailing edge may be inserted rearwardly into said second stirrup. The second tine may also include a detent and the second stirrup may include an opening formed therein to receive the detent such that, to selectively interlock the handle and the impression tray, the detent engages the periphery of the opening when the second tine is inserted into the second stirrup.

In a still further, alternative, the handle securing element may include adhesive that is applied to the ends of the tines during the manufacturing process.

In use, the dentist, orthodontist, or other dental personnel would obtain one of the disposable impression trays from its storage location. The handle would then be attached to the impression tray, either by adhesive or by inserting the tines into the stirrups. The impression tray would then be filled with the impression material and inserted into the mouth of the patient for forming of the impression. Following the formation procedure, the impression tray is removed from the patient's mouth, and the impression material is removed from the tray. At that point, the handle may be disengaged form the impression tray, the impression tray may be disposed of or recycled, and the handle may be disposed of or sterilized for reuse.

By virtue of the foregoing, there is thus provided a single use, dental impression tray and handle assembly that retains the impression material therein without the need for contact cement spray. Additionally, the impression tray has a separate, but readily attachable, handle which facilitates compact shipment and storage, and ease of use. These and other objects and advantages of the present invention shall become apparent from the accompanying drawings and the detailed description thereof.

BRIEF DESCRIPTION OF THE DRAWINGS

The accompanying drawings, which are incorporated in and constitute a part of this specification, illustrate embodiments of the invention and, together with a general description given above, and a detailed description given below, serve to explain the principles of the invention.

FIG. 1 is an exploded perspective view of an upper dental impression tray and handle made in accordance with the principles of the present invention;

FIG. 2 is an assembled perspective view of the dental impression tray and handle of FIG. 1;

DETAILED DESCRIPTION OF THE DRAWINGS

Figure 3:
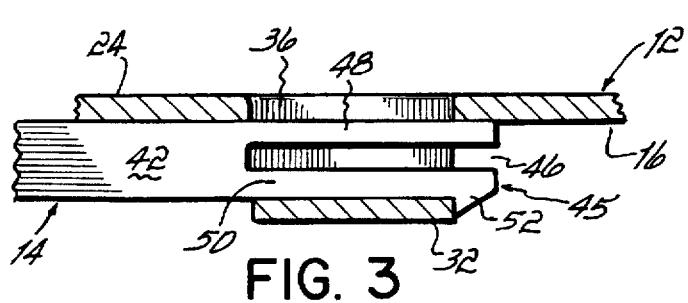
FIG. 3 is a partial sectional view taken along line 3—3 of FIG. 2.

With reference to FIGS. 1 and 2, there is shown a disposable dental impression tray and handle assembly 10 comprising a formable upper dental impression tray 12 (see FIGS. 1–2, and 5), or a formable lower dental impression tray 100 (FIG. 6), and a separate, but readily attachable, handle 14. Impression tray 12, which is of a standard shape and size to be received within the mouth of a patient, includes a tray bottom 16 and a circumferential sidewall 18 extending upwardly along the perimeter of bottom 16. Although impression tray and handle assembly 10 is referred to as a "dental" impression tray, this term is being used as an all inclusive sense to incorporate use by dentists, orthodontists, and any other individuals in the formation of an impression of a person's dental anatomy.

Bottom 16 and sidewall 18 have interior surfaces 20, 22, respectively, which together form the inside surface 24 of impression tray 12. As shown in FIGS. 1 and 2, impression tray 12 is an upper impression tray such that bottom 16 includes a central portion 26, which is of a shape and size to correspond to the roof of the mouth of a patient, and a peripheral portion 28, which corresponds to the shape and size of the bite of a patient. Sidewall 18 extends upwardly about one inch from bottom 16 along the front and side portions. However, it extends upwardly only about one-eighth to one-fourth inch along the rear portion of bottom 16 to form a post dam 30.

Peripheral portion 28 of bottom 16 includes three stirrups 32, 34 for a purpose to be described below. Outer stirrups 32 are symmetric about the longitudinal axis of impression tray 12 and are positioned about midway between the front and back of peripheral portion 28. Central stirrup 34 is positioned on the longitudinal axis and at the front of impression tray 12. Stirrups 32, 34 are formed by stamping a portion of bottom 16 downwardly. Through this process, an aperture 36 is formed in the bottom 16 of impression tray 12. Additionally, stirrups 32, 34 are connected to bottom 16 along the sides, but are open along the front and back (see FIG. 3).

Handle 14 is preferably manufactured from steel and may be for single use or reuse as desired. Handle 14 includes a handgrip 40 and three tines 42, 44, extending forwardly therefrom. Tines 42, 44 are adapted to be received within stirrups 32, 34. To this end, outer tines 42 are of a length greater than central tine 44. Further, tines 42, 44 are of a thickness substantially equal to the distance that stirrups 32, 34 are stamped below bottom 16 of impression tray 12. Thus, tines 42, 44 are receivable within stirrups 32, 34.

To selectively interlock handle 14 to impression tray 12, handle 14 includes a handle securing element 45. Handle securing element 45 may comprise a slot 46 formed in outer tines 42, which divides the ends of outer tines 42 into an upper segment 48 and a lower segment 50. Lower segment 50 further includes a detent 52. Because the detent-containing outer tines 42 are provided with a slotted end 46, detents 52 are effectively cantilevered such that they have a limited degree of resilience. This resilience permits detents 52 to deflect when tines 42 are inserted in stirrups 32, and when fully inserted, to return to their normal non-deflected position, wherein detents 52 engage stirrups 32 and prevent withdrawal of handle 14 from engagement with impression tray 12. To disengage handle 14 from impression tray 12, detents 52 are manually deflected upwardly and tines 42, 44 are withdrawn from stirrups 32, 34.

Additionally, tines 42, 44 are sized such that, when tines 42, 44 are fully inserted within stirrups 32, 34, they fully close apertures 36. Thus, impression material which is placed within impression tray 12 is inhibited from being forced out of apertures 36 during formation of an impression. However, as will be recognized by those skilled in the art, some impression material will be displaced out of the top of the tray during formation of the impression as is common. Nevertheless, the impression material will not be forced through apertures 36 in impression tray 12.

Although handle 14 is shown with three tines 42, 44, differing numbers of tines may be used without departing from the spirit or scope of the present invention. For example, central tine 44 and central stirrup 34 could be eliminated. Moreover, only one tine 42, 44 need include detent 52. It will also be appreciated by those skilled in the art that tines 42, 44 could be formed on impression tray 12 and stirrups 32, 34 could be formed on handle 14.

Figure 5:
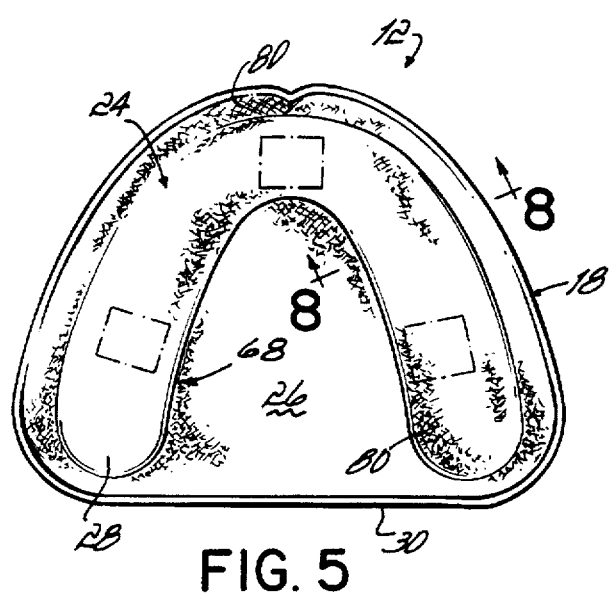
FIG. 5 is a top view of another dental impression tray in accordance with the principles of the present invention having fibers secured to the inside surface.
Figure 6:
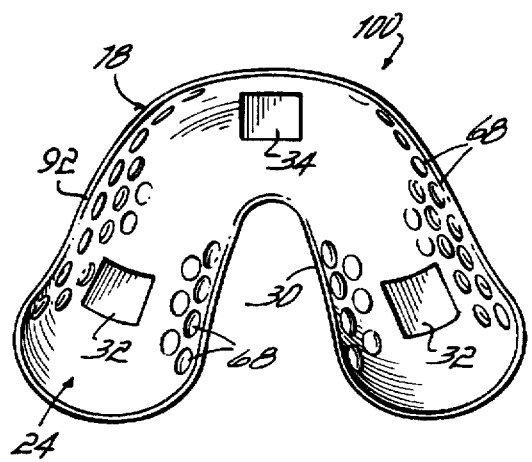
FIG. 6 is a top view similar to FIG. 5, but of a lower dental impression tray made in accordance with the principles of the present invention.
Figure 7:
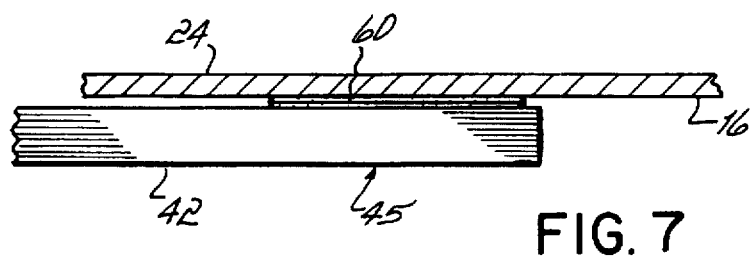
FIG. 7 is a partial sectional view similar to FIG. 3, but with an adhesive strip on the handle for securing the handle to the impression tray.

Alternatively, and as shown in FIGS. 5 and 7, the handle securing element 45 may comprise adhesive strips 60 that are positioned on the distal end of tines 42, 44. Adhesive strips 60 could include a peel-off cover to protect the adhesive strip during storage prior to use. Additionally, adhesive strips 60 may be included on some or all of tines 42, 44, as will be readily apparent to those skilled in the art. Still further, adhesive strips 60 could be positioned during construction on the bottom 16 of impression tray 12, rather than on tines 42, 44.

Figure 9:
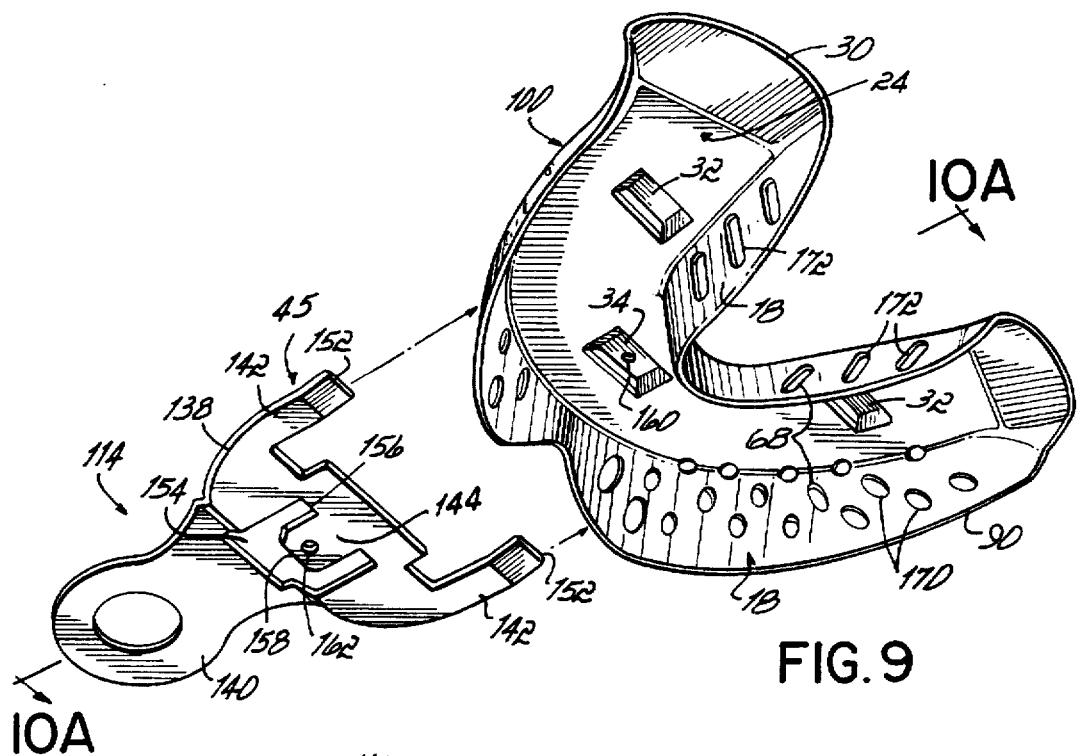
FIG. 9 is an exploded perspective view of another lower dental impression tray and handle made in accordance with the principles of the present invention.
Figure 10A:
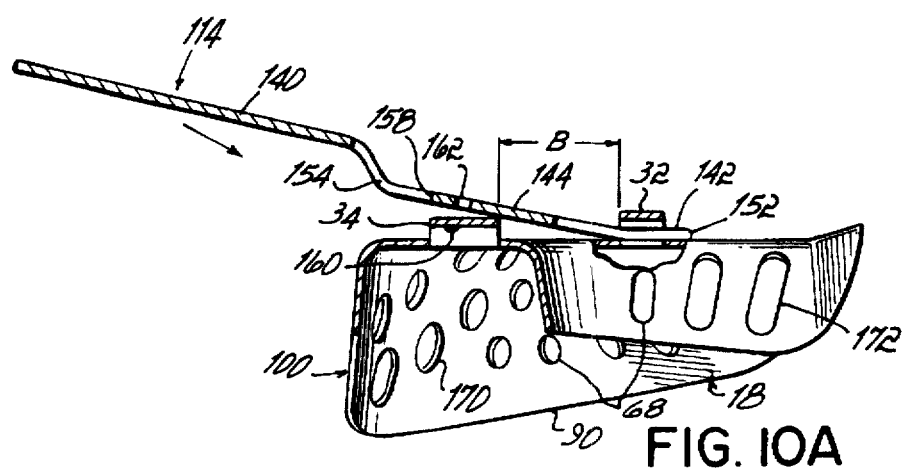
FIG. 10A is a cross-sectional view taken along line 10A—10A of FIG. 9 showing the insertion of the first tine into the first stirrup.
Figure 10B:
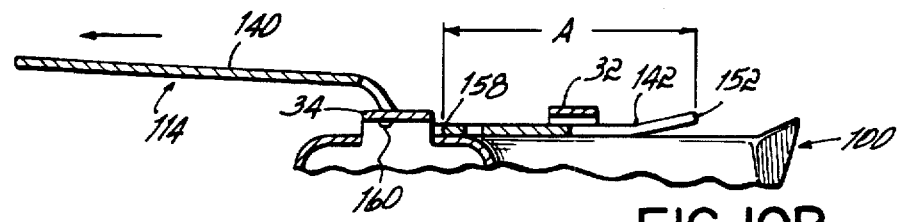
FIG. 10B is a cross-sectional view similar to FIG. 10A, but showing the insertion of the second tine into the second stirrup.
Figure 10C:
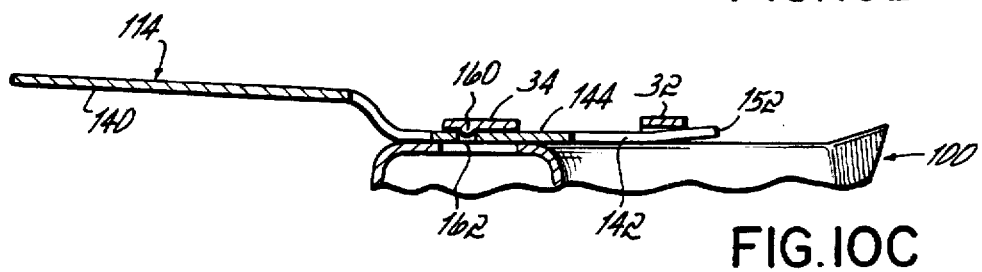
FIG. 10C is a cross-sectional view similar to FIG. 10A, but showing the handle secured to the impression tray.
Figure 11:
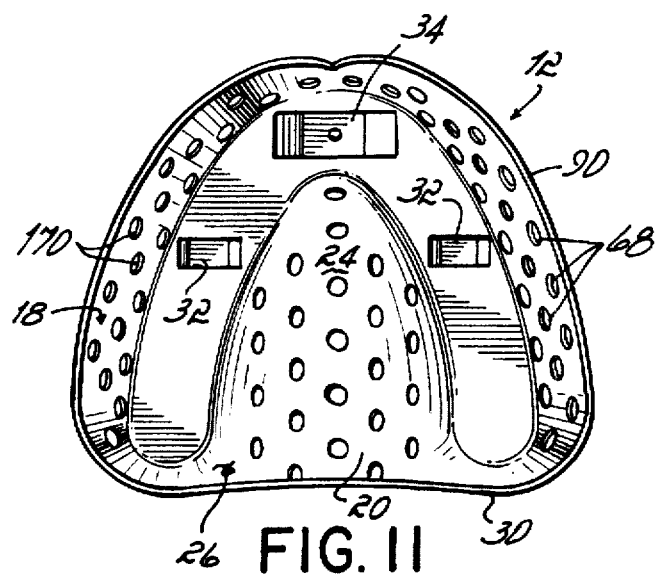
FIG. 11 is a top view of another upper dental impression tray in accordance with the principles of the present invention.

In a still further alternative, and as shown in FIGS. 9–11, handle 114 includes a handle body 138 with a handgrip 140 extending rearwardly therefrom. Handle securing element 45 comprises a pair of outer tines 142 extending forwardly from opposing sides of handle body 138, each of outer tines 142 terminating in a leading edge 152. A generally rectangular recess 154 is formed centrally within handle body 138. Extending rearwardly from the front edge 156 of recess 154 is a centrally positioned tine 144 that terminates in a trailing edge 158. Tines 142, 144 are adapted to be received within stirrups 32, 34, respectively. To that end, outer tines 142 are positioned forwardly of central tine 144. Moreover, the distance between leading edge 152 of outer tines 142 and trailing edge 158 of central tine 144, identified as reference letter A in FIG. 10B, is greater than the smallest distance between stirrups 32, 34, identified as reference letter B in FIG. 10A. To selectively interlock handle 114 and lower dental impression tray 100, outer tines 142 are inserted forwardly into outer stirrups 32 (FIG. 10A) until trailing edge 158 of central tine 144 is positioned forwardly of central stirrup 34 (FIG. 10B). Central tine 144 is then inserted rearwardly into central stirrup 34 (FIG. 10B) until central tine 144 is fully inserted therein (FIG. 10C). To disengage handle 114 from impression tray 100, handle 114 is pushed forwardly until central tine 144 is released from central stirrup 34. Handle 114 is then pulled rearwardly and in a direction away from impression tray 100 to release outer tines 142 from outer stirrups 32.

To assist in the insertion of outer tines 142 into outer stirrups 32, leading edge 152 may be cantilevered in a direction away from impression tray 100. Additionally, the cantilever of outer tines 142 aids in releasably interlocking handle 114 to impression tray 100 by frictionally engaging outer tines 142 with outer stirrups 32.

To further aid in selectively interlocking handle 114 to impression tray 100, central stirrup 34 may include a detent 160 formed thereon with a mating opening 162 formed in central stirrup 144. When central tine 144 is rearwardly inserted into central stirrup 34, detent 160 engages the periphery of opening 162, thereby providing tactile feedback to the user that central tine 144 is fully inserted into central stirrup 34.

Although, as shown, outer tines 142 extend forwardly and central tine 144 extends rearwardly, it will be readily appreciated that the positions and orientations of the tines and stirrups may be changed without departing from the spirit and scope of the present invention. For example, outer tines 142 could be oriented to extend rearwardly with central tine 144 extending forwardly. Further, tines 142, 144 could be formed on impression tray 100 and stirrups 32, 34 could be formed on handle 114. Still further, central tine 144 and central stirrup 34 could be eliminated and the detent 160 and opening 162 transferred to the outer tines 142 and outer stirrups 32.

As shown in FIGS. 1, 2, 4–6, 8–10A and 11, to aid in retaining the impression material within impression tray 12, 100 when impression tray 12, 100 is removed from the mouth of the patient, impression tray 12, 100 includes impression material retaining structure 68. Impression material structure 68 may comprise a plurality of pockets 70 formed in the inside surface 24 of impression tray 12, 100 (FIGS. 1–2, 4 and 6). Pockets 70 are of a generally cylindrical shape, and preferably have an undercut sidewall 72 and further may include a concave base 74. Pockets 70 serve to mechanically retain the impression material within impression tray 12, 100 by providing structure to which the impression material may adhere. Specifically, as impression tray 12, 100 is placed into the mouth of the patient, the impression material is forced into pockets 70, which grip the impression material and also aid in preventing the impression material from being forced away from the mouth structure. Although pockets 70 are shown having a generally cylindrical shape, other shapes may be used. Additionally, although it is preferable that sidewalls 72 be undercut and base 74 be concave, these features are not necessary.

Figure 8:
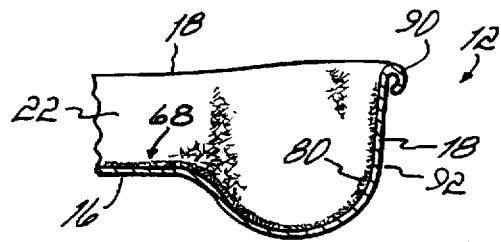
FIG. 8 is a cross-sectional view taken along line 8—8 of FIG. 5 showing the orientation of the fibers relative to the inside surface of the impression tray.

Alternatively, and as best seen in FIGS. 5 and 8, impression material retaining structure 68 may comprise a plurality of fibers 80 secured to inside surface 24 of impression tray 12. In this embodiment, rayon or nylon fibers 80 (or other suitable material) is electrostatically flocked to inside surface 24. To retain fibers 80 to inside surface 24, inside surface 24 is treated with adhesive prior to the flocking process. Because the fibers are electrostatically flocked to inside surface 24, the fibers are oriented substantially perpendicularly to inside surface 24 along the entire extent thereof, as best shown in FIG. 8. Thus, fibers 80 are able to assist in retaining the impression material within impression tray 12.

Preferably, the fibers have a length from about 0.015 inch to about 0.03 inch. However, as will be readily apparent to those skilled in the art, other fiber lengths may be used.

In a further embodiment of the present invention, and as best seen in FIGS. 9 and 11, impression material retention structure 68 may comprise a plurality of apertures 170, 172 formed in the inside surface 24 of impression tray 12, 100. The function of apertures 170, 172 is to permit only as much impression material to be forced therethrough as will retain the impression material in impression tray 12, 100 when the impression material hardens and impression tray 12, 100 is removed from the mouth of the patient. Thus, as will be readily appreciated, the size of apertures 170, 172 is selected as a function of viscosity. The lower the viscosity of the impression material, the smaller apertures 170, 172 should be to limit the amount of impression material that is forced therethrough. Similarly, the higher the viscosity of the impression material, the larger apertures 170, 172 may be. In this regard, it has been found that with a commonly-used impression material, such as the impression material alginate sold by Ormco Corporation, Glendora, Calif. under the name "BASIS", apertures having a length and width of about 0.1 inch to about 0.2 inch serve to adequately retain the impression material within impression tray 12, 100 while limiting the amount of impression material forced through apertures 170, 172.

As a result of the forming process during manufacture of impression tray 12, 100, apertures 170, 172 are generally elliptical in cross-section. In particular, apertures 170 are formed in impression tray 12, 100 as circular openings prior to formation by stamping of the tray into a shape to be received in the mouth of the patient. During the stamping process, apertures 170 are stretched into an elliptical shape that is aligned with the direction of stretching that occurs when impression tray 12, 100 is stamped during manufacture. Apertures 172 in the post dam 30 of impression tray 12, 100, by contrast, are formed as elongated slots in impression tray 12, 100 prior to stamping. Moreover, apertures 172 are oriented in the direction of the stretching of the material of impression tray 12, 100 during the stamping process. This reduces the stress in the material during formation and prevents tearing of impression tray 12, 100 at apertures 172 during the stamping process, which was found to occur when apertures 172 were formed as circular holes prior to stamping.

Impression tray 12, 100 is preferably formed from an anodized aluminum alloy, 1100 series, dead soft, and having a thickness of about 0.025 inch. This material and thickness gives impression tray 12, 100 the necessary rigidity while still permitting the tray to be formed manually by the orthodontist during the impression procedure without the aid of tools. Additionally, being made from aluminum, impression tray 12, 100 is recyclable and need not be discarded as trash after use. However, the invention is not limited to the use of such a material, and other suitably formable and recyclable materials may be used. Moreover, rigid materials may be used for the impression tray 12, 100 without departing from the scope of the present invention.

Figure 4:
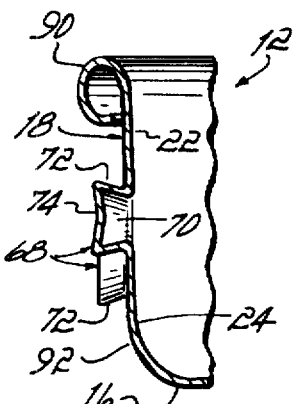
FIG. 4 is a sectional view taken along line 4—4 of FIG. 2.

To improve the safety to the patient of impression tray 12, 100 in use, the upper edges 90 of sidewall 18 may be rolled outwardly to eliminate rough edges (see FIG. 4). Further, because impression tray 12, 100 is intended for single use only, there is no need to sterilize the impression tray after use, thereby reducing risk of spreading infection and also reducing the cost associated with sterilization.

As the size of each patient's oral structure may vary, different sized impression trays 12, 100 may be provided. The impression trays may be color coded to readily indicate the size of the impression tray. For example, in the pocketed and apertured versions, the exterior surface 92 of impression tray 12, 100 could be spray painted different colors. Alternatively, in the flocked version, fibers 80 could be colored differently for different sizes.

Additionally, because impression tray 12, 100 is manufactured without handle 14, 114 it may be stacked with other like-sized impression trays for easy storage. Further, handles 14, 114 may be stored in a bag or similar structure prior to use. Thus, the orthodontist may readily store impression tray 12, 100 and handle 14, 114 and easily retrieve the same when needed.

In use, the dentist, orthodontist, or other dental office personnel would remove impression tray 12, 100 from the suitable storage location and selectively interlock handle 14, 114 thereto, either by slidably inserting the tines into the stirrups as set forth above or by adhesively securing the tines to impression tray 12 by way of adhesive strips 60. Next, the dentist, orthodontist, or other dental office personnel would fill impression tray 12, 100 with impression material and insert the impression tray and handle assembly 10 into the mouth of a patient. Since there are no substantial openings, perforations, or the like in the sidewalls or bottom of the impression tray 12, 100 when the handle 14, 114 is engaged therewith, the impression material is inhibited from being hydraulically forced through such sidewall and/or bottom openings, perforations or the like of impression tray 12, 100 when the impression is made. However, some incidental material will be urged upwardly above the original level of the impression material in the tray or through apertures 170, 172 as the teeth move toward the bottom of the tray, during the impression-making process. Nevertheless, a good impression is assured of the teeth alone or in combination with the gums and the vestibular anatomy. Following formation of the impression of the patient's oral anatomy (i.e., when the impression material has set), the dentist, orthodontist, or other dental office personnel removes impression tray and handle assembly 10 from the mouth of the patient, the impression material retention structure 68 serving to retain the impression material in impression tray 12, 100. The impression material may then be removed from the impression tray and the entire impression tray and handle assembly 10 disposed of in any acceptable manner. However, handle 14, 114 may be detached from impression tray 12, 100 and reused if desired. Further, impression tray 12, 100 may be recycled rather than discarded as ordinary trash.

By virtue of the foregoing, there is thus provided a single use, formable dental impression tray and handle assembly that retains the impression material therein without the need for contact cement spray. Additionally, the impression tray is manually deformable and may be freely stacked for storage and ease of use. Finally, the separate, but readily attachable, handle facilitates storage, compact shipment, and ease of use.

While the present invention has been illustrated by description of different embodiments which have been described in considerable detail, it is not the intention of the applicant to restrict or in any way limit the scope of the appended claims to such detail. Additional advantages will readily appear to those skilled in the art. For example, impression tray 12, 100 may be used without handle 14, 114. In that event, impression tray 12, 100 would not include stirrups 32, 34 or attachment locations for handle 14, 114 by way of adhesive. Alternatively, impression tray 12, 100 may have handle 14, 114 integrally formed therewith or rigidly fixed thereto. Thus, the invention in its broadest aspects is not limited to the specific details, representative apparatus and method, and illustrative examples shown and described.

Accordingly, departures may be made from the details without departing from the spirit or scope of applicant's general inventive concept.

What is claimed is:

1. A single-use impression tray assembly comprising:

a dental impression tray, said impression tray having a bottom and a peripheral sidewall extending upwardly from said bottom, each of said sidewall and said bottom including an interior surface, said interior surfaces forming the inside surface of said impression tray, said impression tray being manually deformable during the impression procedure without the use of tools to conform the shape of said impression tray to the shape of a patient's oral anatomy;

impression material retaining structure formed in said inside surface of said impression tray to provide mechanical retention between said impression tray and the impression material;

a separate, but readily attachable handle; and a plurality of tines formed on one of said handle and said impression tray and a plurality of mating stirrups for receiving said tines therein formed on the other one of said handle and said impression tray to selectively interlock said impression tray and said handle, said plurality of tines and said plurality of mating stirrups inhibiting disengagement of said handle from said impression tray during normal use in the impression forming procedure.

2. The impression tray of claim 1 wherein there are two outer tines and one centrally positioned tine, and two outer stirrups and one centrally positioned stirrup, each of said outer tines including an upper segment and a resilient lower segment having a detent that engages with a corresponding outer stirrup when said outer tines are inserted into said outer stirrups to selectively interlock said handle and said impression tray.

3. The impression tray of claim 2 wherein said plurality of tines is formed on said handle and said plurality of stirrups is formed on said impression tray.

4. The impression tray of claim 1 wherein a first tine of said plurality of tines is positioned forwardly of a second tine of said plurality of tines, said first tine extending forwardly and terminating in a leading edge, said first tine to be received in a first stirrup of said plurality of stirrups, and said second tine extending rearwardly and terminating in a trailing edge, said second tine to be received in a second stirrup of said plurality of stirrups.

5. The impression tray of claim 4, wherein the distance between said leading edge and said trailing edge is greater than the smallest distance between said first stirrup and said second stirrup, whereby to selectively interlock said handle and said impression tray, said first tine is inserted forwardly into said first stirrup until said trailing edge may be inserted rearwardly into said second stirrup.

6. The impression tray of claim 5, said second stirrup further including a detent and said second tine including an opening formed therein to receive said detent, said detent engaging the periphery of said opening when said second tine is inserted into said second stirrup to selectively interlock said handle and said impression tray.

7. The impression tray of claim 6 wherein there are two of said first tine and one of said second tine, said second tine being positioned centrally of said first tines.

8. The impression tray of claim 7 wherein said tines are formed on said handle and said stirrups are formed on said impression tray.

9. A single-use impression tray assembly comprising:

a dental impression tray, said impression tray having a bottom and a peripheral sidewall extending upwardly from said bottom, each of said sidewall and said bottom including an interior surface, said interior surfaces forming the inside surface of said impression tray, said impression tray being manually deformable during the impression procedure without the use of tools to conform the shape of said impression tray to the shape of a patient's oral anatomy:

impression material retaining structure formed in said inside surface of said impression tray to provide mechanical retention between said impression tray and the impression material;

a separate, but readily attachable handle; and a plurality of tines formed on said handle and adhesive strips secured to one of said tines and said impression tray for selectively interlocking said handle to said impression tray, said handle securing element inhibiting disengagement of said handle from said impression tray during normal use in the impression forming procedure.

10. A single-use impression tray assembly comprising:

a dental impression tray, said impression tray having a bottom and a peripheral sidewall extending upwardly from said bottom, each of said sidewall and said bottom including an interior surface, said interior surfaces forming the inside surface of said impression tray;

impression material retaining structure formed in said inside surface of said impression tray to provide mechanical retention between said impression tray and the impression material;

a separate, but readily attachable handle having a plurality of tines; and a plurality of stirrups formed in said impression tray by stamping a portion of said bottom of said impression tray a distance sufficient to receive said tines therebetween, said stamped portions forming apertures in said bottom, said tines mating with said apertures when said tines are inserted into said stirrups to inhibit impression material from being hydraulically forced from said apertures during the impression procedure, at least one of said tines including an upper segment and a resilient lower segment having a detent, said detent engaging one of said stirrups when said tine is inserted therein to selectively interlock said handle and said impression tray.

11. A single-use impression tray assembly comprising:

a dental impression tray, said impression tray having a bottom and a peripheral sidewall extending upwardly from said bottom, each of said sidewall and said bottom including an interior surface, said interior surfaces forming the inside surface of said impression tray;

impression material retaining structure formed in said inside surface of said impression tray to provide mechanical retention between said impression tray and the impression material;

a separate, but readily attachable handle having a plurality of tines, a first tine of said plurality of tines positioned forwardly of a second tine of said plurality of tines, said first tine extending forwardly and terminating in a leading edge and said second tine extending rearwardly and terminating in a trailing edge; and a plurality of stirrups formed in said impression tray, a first stirrup of said plurality of stirrups positioned to receive said first tine and a second stirrup of said plurality of stirrups positioned to receive said second tine, the distance between said leading edge and said trailing edge being greater than the smallest distance between said first stirrup and said second stirrup, whereby to selectively interlock said handle and said impression tray, said first tine is inserted forwardly into said first stirrup until said trailing edge may be inserted rearwardly into said second stirrup.

12. The impression tray of claim 11, said second stirrup further including a detent and said second tine including an opening formed therein to receive said detent, said detent engaging the periphery of said opening when said second tine is inserted into said second stirrup to selectively interlock said handle and said impression tray.

13. The impression tray of claim 12 wherein there are two of said first tine and one of said second tine, said second tine being positioned centrally of said first tines.

14. A method of making a dental impression, comprising:
providing a dental impression tray having one of a plurality of stirrups and a plurality of tines;
providing a separate, but readily attachable handle having the other one of said plurality of stirrups and said plurality of tines, at least one of said plurality of tines including an upper segment and a resilient lower segment having a detent;
inserting said plurality of tines into said plurality of stirrups, said detent engaging one of said plurality of stirrups when said at least one tine is inserted therein to selectively interlock said handle and said impression tray;
filling said impression tray with impression material;
inserting said impression tray into the mouth of a patient; and
removing said impression tray from the mouth of the patient after the impression material has set.

15. The method of making an impression of claim 14 further comprising removing said impression material from said impression tray after said impression tray is removed from the mouth of the patient.

16. The method of making an impression of claim 15 further comprising disposing of said impression tray and handle.

17. The method of making an impression of claim 14 further comprising detaching said handle from said impression tray.

18. The method of making an impression of claim 17 further comprising recycling said impression tray.

19. The method of making an impression of claim 17 further comprising sterilizing said handle for reuse with another said impression tray.

20. A method of making a dental impression, comprising:
providing a dental impression tray having one of a plurality of tines and a plurality of stirrups;
providing a handle having the other one of said plurality of tines and said plurality of stirrups, a first tine of said plurality of tines positioned forwardly of a second tine of said plurality of tines, said first tine extending forwardly and terminating in a leading edge and said second tine extending rearwardly and terminating in a trailing edge, a first stirrup of said plurality of stirrups positioned to receive said first tine and a second stirrup of said plurality of stirrups positioned to receive said second tine, the distance between said leading edge and said trailing edge being greater than the smallest distance between said first stirrup and said second stirrup;
inserting said first tine forwardly into said first stirrup until said trailing edge may be inserted rearwardly into said second stirrup;
inserting said trailing edge rearwardly into said second stirrup to selectively interlock said impression tray and said handle;
filling said impression tray with impression material;
inserting said impression tray into the mouth of a patient; and
removing said impression tray from the mouth of the patient after the impression material has set.

21. The method of making an impression of claim 20 wherein said second stirrup includes a detent and said second tine includes an opening formed therein to receive said detent, said method further comprising inserting said trailing edge rearwardly into said second stirrup until said detent engages the periphery of said opening to selectively interlock said handle and said impression tray.

22. The method of making an impression of claim 20 further comprising removing said impression material from said impression tray after said impression tray is removed from the mouth of the patient.

23. The method of making an impression of claim 22 further comprising disposing of said impression tray and handle.

24. The method of making an impression of claim 20 further comprising detaching said handle from said impression tray.

25. The method of making an impression of claim 24 further comprising recycling said impression tray.

26. The method of making an impression of claim 24 further comprising sterilizing said handle for reuse with another said impression tray.

27. A single-use impression tray assembly comprising:
a dental impression tray, said impression tray having a bottom and a peripheral sidewall extending upwardly from said bottom, each of said sidewall and said bottom including an interior surface, said interior surfaces forming the inside surface of said impression tray;
impression material retaining structure formed in said inside surface of said impression tray to provide mechanical retention between said impression tray and the impression material; and
a separate, but readily attachable handle having a plurality of tines, said handle selectively interlocked to said impression tray by adhesive strips secured to one of said tines and said impression tray.

28. A single-use impression tray assembly comprising:
a dental impression tray, said impression tray having a bottom and a peripheral sidewall extending upwardly from said bottom, each of said sidewall and said bottom including an interior surface, said interior surfaces forming the inside surface of said impression tray;
impression material retaining structure formed in said inside surface of said impression tray to provide mechanical retention between said impression tray and the impression material; and
a separate, but readily attachable handle; and
a plurality of tines formed on one of said handle and said impression tray and a plurality of mating stirrups for receiving said tines formed on the other one of said handle and said impression tray, wherein to selectively interlock said impression tray and said handle a first tine of said plurality of tines is positioned forwardly of a second tine of said plurality of tines, said first tine extending forwardly and terminating in a leading edge, said first tine to be received in a first stirrup of said plurality of stirrups, and said second tine extending rearwardly and terminating in a trailing edge, said second tine to be received in a second stirrup of said plurality of stirrups.

29. The impression tray of claim 28 wherein the distance between said leading edge and said trailing edge is greater than the smallest distance between said first stirrup and said second stirrup, whereby to selectively interlock said handle and said impression tray, said first tine is inserted forwardly into said first stirrup until said trailing edge may be inserted rearwardly into said second stirrup.

30. The impression tray of claim 29, said second stirrup further including a detent and said second tine including an opening formed therein to receive said detent, said detent engaging the periphery of said opening when said second tine is inserted into said second stirrup to selectively interlock said handle and said impression tray.

31. The impression tray of claim 30 wherein there are two of said first tine and one of said second tine, said second tine being positioned centrally of said first tines.

32. The impression tray of claim 31 wherein said tines are formed on said handle and said stirrups are formed on said impression tray.

* * * * *